(12) United States Patent
Cazares

(10) Patent No.: US 7,725,184 B2
(45) Date of Patent: May 25, 2010

(54) CARDIAC TACHYARRHYTHMIA THERAPY SELECTION BASED ON PATIENT RESPONSE INFORMATION

(75) Inventor: Shelley Marie Cazares, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 408 days.

(21) Appl. No.: 11/807,696

(22) Filed: May 30, 2007

(65) Prior Publication Data

US 2007/0239217 A1 Oct. 11, 2007

Related U.S. Application Data

(63) Continuation of application No. 10/995,655, filed on Nov. 23, 2004, now Pat. No. 7,228,173.

(51) Int. Cl.
*A61N 1/362* (2006.01)
(52) U.S. Cl. .................. 607/14; 600/509; 600/510; 600/518; 607/4; 607/9
(58) Field of Classification Search ......... 600/509–510, 600/518; 607/4, 9, 14
See application file for complete search history.

(56) References Cited

U.S. PATENT DOCUMENTS

| | | | |
|---|---|---|---|
| 4,023,564 A | 5/1977 | Valiquette et al. |
| 4,336,810 A | 6/1982 | Anderson et al. |
| 4,428,378 A | 1/1984 | Anderson et al. |
| 4,550,221 A | 10/1985 | Mabusth |
| 4,686,332 A | 8/1987 | Greanias et al. |
| 4,830,006 A | 5/1989 | Haluska et al. |
| 4,865,036 A | 9/1989 | Chirife |
| 4,872,459 A | 10/1989 | Pless et al. |
| 4,880,005 A | 11/1989 | Pless et al. |

(Continued)

FOREIGN PATENT DOCUMENTS

EP 0 450 943 1/1996

(Continued)

OTHER PUBLICATIONS

U.S. Appl. No. 10/955,831, filed Sep. 30, 2004, Kim et al.

(Continued)

*Primary Examiner*—Carl H Layno
*Assistant Examiner*—Deborah Malamud
(74) *Attorney, Agent, or Firm*—Hollingsworth & Funk, LLC

(57) ABSTRACT

Cardiac treatment methods and devices providing templates representative of past tachyarrhythmia events, each template associated with a therapy. A cardiac waveform is detected, and if it corresponds to a particular template associated with a previous therapy that was satisfactory in terminating a past event, the previous therapy is delivered again. If unsatisfactory, the previous therapy is eliminated as an option. If, for example, the previous therapy was an antitachycardia pacing therapy unsatisfactory in terminating the past tachyarrhythmia event, delivery of the antitachycardia pacing therapy is eliminated as an option. Instead of ATP therapy, one or more of a cardioversion, defibrillation, or alternate anti-tachycardia pacing therapy may be associated with the particular template. Cardiac waveforms and templates may correspond in terms of one or more of morphology, timing, drug regimen, medication, neural activity, patient activity, hemodynamic status, cardiac tissue impedance, transthoracic impedance, or other information corresponding to the episode.

24 Claims, 9 Drawing Sheets

U.S. PATENT DOCUMENTS

| | | |
|---|---|---|
| 5,002,052 A | 3/1991 | Haluska |
| 5,107,850 A | 4/1992 | Olive |
| 5,144,947 A | 9/1992 | Wilson |
| 5,158,092 A | 10/1992 | Glace |
| 5,161,527 A | 11/1992 | Nappholz et al. |
| 5,161,529 A | 11/1992 | Stotts et al. |
| 5,176,137 A | 1/1993 | Erickson et al. |
| 5,181,511 A | 1/1993 | Nickolls et al. |
| 5,193,550 A | 3/1993 | Duffin |
| 5,209,229 A | 5/1993 | Gilli |
| 5,217,021 A | 6/1993 | Steinhaus et al. |
| 5,222,493 A | 6/1993 | Sholder |
| 5,224,475 A | 7/1993 | Berg et al. |
| 5,251,624 A | 10/1993 | Bocek et al. |
| 5,257,621 A | 11/1993 | Bardy et al. |
| 5,312,441 A | 5/1994 | Mader et al. |
| 5,312,445 A | 5/1994 | Nappholz et al. |
| 5,324,310 A | 6/1994 | Greeninger et al. |
| 5,330,505 A | 7/1994 | Cohen |
| 5,330,508 A | 7/1994 | Gunderson |
| 5,342,402 A | 8/1994 | Olson et al. |
| 5,350,410 A | 9/1994 | Kleks et al. |
| 5,379,776 A | 1/1995 | Murphy et al. |
| 5,411,031 A | 5/1995 | Yomtov |
| 5,425,749 A | 6/1995 | Adams |
| 5,447,519 A | 9/1995 | Peterson |
| 5,458,620 A | 10/1995 | Adams et al. |
| 5,472,453 A | 12/1995 | Alt |
| 5,513,644 A | 5/1996 | McClure et al. |
| 5,548,619 A | 8/1996 | Horiike et al. |
| 5,554,177 A | 9/1996 | Kieval |
| 5,587,970 A | 12/1996 | Greenwood |
| 5,662,688 A | 9/1997 | Haefner et al. |
| 5,683,424 A | 11/1997 | Brown et al. |
| 5,683,431 A | 11/1997 | Wang |
| 5,685,315 A | 11/1997 | McClure et al. |
| 5,725,559 A | 3/1998 | Alt et al. |
| 5,755,737 A | 5/1998 | Prieve et al. |
| 5,779,645 A | 7/1998 | Olson et al. |
| 5,782,888 A | 7/1998 | Olson et al. |
| 5,817,027 A | 10/1998 | Arand et al. |
| 5,836,971 A | 11/1998 | Starkweather |
| 5,844,506 A | 12/1998 | Binstead |
| 5,846,263 A | 12/1998 | Peterson et al. |
| 5,855,593 A | 1/1999 | Olson et al. |
| 5,857,977 A | 1/1999 | Caswell et al. |
| 5,871,512 A | 2/1999 | Hemming et al. |
| 5,893,882 A | 4/1999 | Peterson et al. |
| 5,978,707 A | 11/1999 | Krig et al. |
| 5,999,854 A | 12/1999 | White |
| 6,064,906 A | 5/2000 | Langberg et al. |
| 6,076,014 A | 6/2000 | Alt |
| 6,101,414 A | 8/2000 | Kroll |
| 6,128,529 A | 10/2000 | Esler |
| 6,137,308 A | 10/2000 | Nayak |
| 6,147,680 A | 11/2000 | Tareev |
| 6,151,524 A | 11/2000 | Krig et al. |
| 6,167,308 A | 12/2000 | DeGroot |
| 6,178,350 B1 | 1/2001 | Olson et al. |
| 6,185,459 B1 | 2/2001 | Mehra et al. |
| 6,192,273 B1 | 2/2001 | Igel et al. |
| 6,192,275 B1 | 2/2001 | Zhu et al. |
| 6,212,428 B1 | 4/2001 | Hsu et al. |
| 6,221,011 B1 | 4/2001 | Bardy |
| 6,223,078 B1 | 4/2001 | Marcovecchio |
| 6,230,055 B1 | 5/2001 | Sun et al. |
| 6,253,102 B1 | 6/2001 | Hsu et al. |
| 6,266,554 B1 | 7/2001 | Hsu et al. |
| 6,270,457 B1 | 8/2001 | Bardy |
| 6,275,732 B1 | 8/2001 | Hsu et al. |
| 6,277,072 B1 | 8/2001 | Bardy |
| 6,280,380 B1 | 8/2001 | Bardy |
| 6,289,248 B1 | 9/2001 | Conley et al. |
| 6,308,095 B1 | 10/2001 | Hsu et al. |
| 6,312,378 B1 | 11/2001 | Bardy |
| 6,336,903 B1 | 1/2002 | Bardy |
| 6,358,203 B2 | 3/2002 | Bardy |
| 6,368,284 B1 | 4/2002 | Bardy |
| 6,393,316 B1 | 5/2002 | Gillberg et al. |
| 6,398,728 B1 | 6/2002 | Bardy |
| 6,400,986 B1 | 6/2002 | Sun |
| 6,418,340 B1 | 7/2002 | Conley et al. |
| 6,434,417 B1 | 8/2002 | Lovett |
| 6,438,407 B1 | 8/2002 | Ousdigian et al. |
| 6,438,410 B2 | 8/2002 | Hsu et al. |
| 6,440,066 B1 | 8/2002 | Bardy |
| 6,445,949 B1 | 9/2002 | Kroll |
| 6,449,503 B1 | 9/2002 | Hsu |
| 6,477,422 B1 | 11/2002 | Splett |
| 6,480,734 B1 | 11/2002 | Zhang et al. |
| 6,487,443 B2 | 11/2002 | Olson et al. |
| 6,490,478 B1 | 12/2002 | Zhang et al. |
| 6,564,106 B2 | 5/2003 | Guck et al. |
| 6,594,523 B1 | 7/2003 | Levine |
| 6,611,713 B2 | 8/2003 | Schauerte |
| 6,631,290 B1 | 10/2003 | Guck et al. |
| 6,636,764 B1 | 10/2003 | Fain et al. |
| 6,654,639 B1 | 11/2003 | Lu |
| 6,684,100 B1 | 1/2004 | Sweeney et al. |
| 6,708,058 B2 | 3/2004 | Kim et al. |
| 6,731,982 B1 | 5/2004 | Kroll et al. |
| 6,766,194 B1 | 7/2004 | Kroll |
| 6,801,806 B2 | 10/2004 | Sun et al. |
| 6,882,883 B2 | 4/2005 | Condie et al. |
| 6,885,890 B2 | 4/2005 | Spinelli et al. |
| 6,888,538 B2 | 5/2005 | Ely et al. |
| 6,889,079 B2 | 5/2005 | Bocek et al. |
| 6,909,916 B2 | 6/2005 | Spinelli |
| 6,922,585 B2 | 7/2005 | Zhou |
| 6,993,385 B1 | 1/2006 | Routh |
| 7,031,764 B2 | 4/2006 | Schwartz et al. |
| 7,031,771 B2 | 4/2006 | Brown et al. |
| 7,076,289 B2 | 7/2006 | Sakar et al. |
| 7,085,599 B2 | 8/2006 | Kim et al. |
| 6,084,253 A1 | 9/2006 | Johnson et al. |
| 7,103,405 B2 | 9/2006 | Sakar et al. |
| 7,107,098 B2 | 9/2006 | Sharma et al. |
| 7,129,935 B2 | 10/2006 | Mackey |
| 7,130,677 B2 | 10/2006 | Brown et al. |
| 7,184,815 B2 | 2/2007 | Kim et al. |
| 7,228,173 B2 | 6/2007 | Cazares |
| 7,277,747 B2 | 10/2007 | Cazares et al. |
| 7,330,757 B2 | 2/2008 | Ostroff et al. |
| 7,477,932 B2 | 1/2009 | Lee et al. |
| 7,558,623 B2 | 7/2009 | Fischell et al. |
| 2002/0183637 A1 | 12/2002 | Kim et al. |
| 2003/0120316 A1 | 6/2003 | Spinelli et al. |
| 2003/0191403 A1 | 10/2003 | Zhou et al. |
| 2004/0093035 A1 | 5/2004 | Schwartz et al. |
| 2004/0111119 A1 | 6/2004 | Sakar |
| 2004/0111120 A1 | 6/2004 | Sakar |
| 2004/0111121 A1 | 6/2004 | Brown |
| 2004/0167579 A1 | 8/2004 | Sharma et al. |
| 2004/0176694 A1 | 9/2004 | Kim et al. |
| 2004/0215092 A1 | 10/2004 | Fischell et al. |
| 2004/0215270 A1 | 10/2004 | Ritscher et al. |
| 2005/0131476 A1 | 6/2005 | Kim et al. |
| 2005/0137485 A1 | 6/2005 | Cao et al. |
| 2005/0137641 A1 | 6/2005 | Naughton |
| 2005/0192506 A1 | 9/2005 | Kim et al. |
| 2005/0288600 A1 | 12/2005 | Zhang et al. |
| 2006/0069322 A1 | 3/2006 | Zhang et al. |
| 2006/0074331 A1 | 4/2006 | Kim et al. |
| 2006/0111747 A1 | 5/2006 | Cazares et al. |

| | | | |
|---|---|---|---|
| 2006/0253044 | A1 | 11/2006 | Zhang et al. |
| 2006/0281998 | A1 | 12/2006 | Li |
| 2007/0049974 | A1 | 3/2007 | Li et al. |

FOREIGN PATENT DOCUMENTS

| | | |
|---|---|---|
| EP | 0709112 | 5/1996 |
| EP | 0801960 | 10/1997 |
| EP | 0 547 733 | 4/1998 |
| EP | 1 267 993 | 1/2005 |
| EP | 0360412 | 3/2005 |
| EP | 1112755 | 9/2005 |
| WO | WO9840122 | 9/1998 |
| WO | WO 02/24276 | 3/2002 |
| WO | WO 03/047690 | 6/2003 |
| WO | WO 2006/039694 | 4/2006 |
| WO | WO2006039694 | 4/2006 |

OTHER PUBLICATIONS

U.S. Appl. No. 10/995,655, filed Nov. 23, 2004, Cazares.
U.S. Appl. No. 10/995,704, filed Nov. 23, 2004, Cazares et al.
U.S. Appl. No. 10/996,340, filed Nov. 23, 2004, Cazares.
U.S. Appl. No. 11/038,996, filed Jan. 20, 2005, Li.
U.S. Appl. No. 11/089,185, filed Mar. 24, 2005, Kim et al.
U.S. Appl. No. 11/151,102, filed Jun. 13, 2005, Li.
U.S. Appl. No. 11/209,976, filed Aug. 23, 2005, Li et al.
"VITALITY 2 Implantable Cardioverter Defibrillator System Guide", Guidant Corporation, 2004, Cover pages and pp. 3-15 to 3-19.
Gold, Michael R., et al., "Advanced Rhythm Discrimination for Implantable Cardioverter Defibrillators Using Electrogram Vector Timing and Correlation", *Journal of Cardiovascular Electrophysiology*, vol. 13, No. 11, Nov. 2002, pp. 1092-1097.
Lake et al., *Am. J. Physiol. Requl. Integr. Comp. Physiol.*, 283: R789-97 (2002).
Richman et al., *Am. J. Physiol. Heart Circ. Physiol.*, 278: H2039-49 (2000).
M. S. Wathen, M.D. et al. "Shock Reduction Using Antitachycardia Pacing for Spontaneous Rapid Ventricular Tachycardia in Patients with Coronary Artery Disease", *Circulation 2001*, vol. 104:796-801.
Martha Kerr, "Shock Rate Cut 70% with ICDs Programmed to First Deliver Antitachycardia Pacing: Results of the PainFREE Rx II Trial" *NewsRhythms*, MedScape CRM News 2003. www.medscape.com.
U.S. Appl. No. 11/312,280, filed Dec. 20, 2005, Cazares et al.
U.S. Appl. No. 11/312,279, filed Dec. 20, 2005, Cazares et al.
Dubin, Rapid Interpretation of EKG's, 2000, Cover Publishing Company, $6^{th}$ Edition, p. 334-345.
Office Action from U.S. Appl. No. 11/089,185 dated Nov. 3, 2009, 7 pages.
Office Action from U.S. Appl. No. 11/209,976 dated Nov. 20, 2009, 11 pages.
Mercando et al., Measurement of Differences in Timing and Sequence Between Two Ventricular Electrodes as a Means of Tachycardia Differentiation, PACE, Part II, vol. 9, Nov.-Dec. 1986, 1069-1078. (abstract only).
Office Action from U.S. Appl. No. 11/089,185 dated May 15, 2009, 11 pages.
Office Action from U.S. Appl. No. 11/089,185 dated Dec. 8, 2008, 8 pages.
Office Action from U.S. Appl. No. 11/089,185 dated Mar. 28, 2008, 14 pages.

CARDIAC TACHYARRHYTHMIA THERAPY SELECTION BASED ON PATIENT RESPONSE INFORMATION

RELATED PATENT DOCUMENTS

This application is a continuation of U.S. patent application Ser. No. 10/995,655 filed on Nov. 23, 2004, issued as U.S. Pat. No. 7,228,173 on Jun. 5, 2007, to which Applicant claims priority under 35 U.S.C. §120, and which is incorporated herein by reference in its entirety.

FIELD OF THE INVENTION

The present invention relates generally to patient internal medical devices and methods and, more particularly, to patient internal medical devices and methods that select tachyarrhythmia therapy based on previous patient therapy responses.

BACKGROUND OF THE INVENTION

Proper cardiac function relies on the synchronized contractions of the heart at regular intervals. When the heart is functioning normally, synchronized cardiac contractions are initiated at the sinoatrial node and the heart is said to be operating in normal sinus rhythm. However, if contractions of the heart become irregular or uncoordinated, or if the contraction rate is too fast or too slow, the heart rhythm is described as arrhythmic. Cardiac arrhythmia may be caused, for example, by disease processes or from aberrant electrical conduction patterns occurring in the heart tissue. Cardiac arrhythmia impairs cardiac pumping efficiency and some types of cardiac arrhythmia can be life threatening.

A cardiac arrhythmia that originates in an atrial region of the heart is denoted a supra-ventricular tachyarrhythmia (SVT). Atrial fibrillation and atrial flutter are examples of SVT. Both conditions are characterized by rapid, uncoordinated contractions of the atria resulting in hemodynamically inefficient pumping action.

Another example of SVT is sinus tachycardia, which is an increased heart rate due to exercise or a quick emotional response. In contrast to atrial fibrillation and atrial flutter, sinus tachycardia is characterized by rapid, coordinated contractions of the atria resulting in hemodynamically efficient pumping action, compensating for the increased strain placed upon the body during exercise or quick emotional responses. Whereas atrial fibrillation and atrial flutter are "abnormal" (yet not lethal), sinus tachycardia is "normal" (and also not lethal).

Cardiac arrhythmias originating in a ventricular region of the heart are denoted ventricular tachyarrhythmias. Ventricular tachycardia (VT) is characterized by rapid ventricular contractions and can degenerate into ventricular fibrillation (VF). Ventricular fibrillation produces extremely rapid, non-coordinated contractions of the ventricles. Ventricular fibrillation is fatal unless the heart is returned to sinus rhythm within a few minutes.

Implantable cardiac rhythm management (CRM) devices, including pacemakers and implantable cardioverter/defibrillators, have been used to deliver effective treatment to patients with serious cardiac arrhythmias. Cardiac rhythm management devices may treat cardiac arrhythmias with a variety of tiered therapies. These tiered therapies range from delivering low energy pacing pulses timed to assist the heart in maintaining pumping efficiency to providing high-energy shocks to treat and/or terminate fibrillation. To effectively deliver these treatments, the CRM must first identify the type of arrhythmia that is occurring, after which appropriate therapy may be delivered to the heart.

SUMMARY OF THE INVENTION

The present invention is directed to methods and systems for selecting tachyarrhythmia therapy based on previous patient therapy responses. Methods in accordance with the present invention involve providing one or more templates representative of one or more of a patient's past tachyarrhythmia events, each of the templates associated with a therapy to treat tachyarrhythmia events. A cardiac waveform is detected, and if the cardiac waveform corresponds to a particular template of the one or more templates, a determination is made to see if a previous therapy associated with the particular template was satisfactory in terminating a past tachyarrhythmia event. If the previously delivered therapy was determined satisfactory, the previous therapy is delivered again. If the previously delivered therapy was determined unsatisfactory, the previous therapy is eliminated as an option for treating a subsequent tachyarrhythmia event associated with the particular template.

In further embodiments, if the previous therapy was an antitachycardia pacing therapy determined to be unsatisfactory in terminating the past tachyarrhythmia event, delivery of the antitachycardia pacing therapy for treating a subsequent tachyarrhythmia event is eliminated as an option. Instead of ATP therapy, one or more of a cardioversion, a defibrillation therapy, or an alternate anti-tachycardia pacing therapy may be associated with the particular template.

The correspondence between the cardiac waveform and the particular template may be a correspondence in terms of one or more of morphology, timing, drug regimen, medication information, neural activity information, patient activity information, hemodynamic status information, cardiac tissue impedance information, transthoracic impedance information, respiratory information (e.g., patient disordered breathing information), or other information corresponding to the episode.

A new template may be added to the one or more templates by replacing an oldest template of the one or more templates with the new template. A particular template may be deleted if the particular template is older than a predetermined age, or has not corresponded to a cardiac waveform for a predetermined time, or has corresponded to past arrhythmias less frequently relative to other templates, or represents a heart-rate similar to other existing templates. A particular template may also be deleted if the particular template is associated with a drug regimen that no longer matches the patient's current drug regimen.

The detected cardiac waveform may be indicative of an arrhythmia in the ventricles, of ventricular or supra-ventricular origin, or may be indicative of an arrhythmia in the atria. Arbitrating between two or more templates may be done if the cardiac waveform corresponds to two or more templates. Arbitration may involve: selecting a most recently used or generated template associated with a treatment satisfactory in terminating the past tachyarrhythmia event, and delivering its associated tachyarrhythmia therapy; selecting a template of the two or more templates associated with a treatment satisfactory in terminating the past tachyarrhythmia event, and delivering its associated tachyarrhythmia therapy; selecting the most frequently matched template associated with a treatment satisfactory in terminating the past tachyarrhythmia event, and delivering its associated tachyarrhythmia therapy; selecting the template associated with a treatment satisfactory in terminating the past tachyarrhythmia event whose rate information most closely corresponds to the detected cardiac waveform, and delivering its associated tachyarrhythmia therapy; and/or selecting the template associated with one or more of a patient's drug regimen, neural activity, patient activity, hemodynamic state, transthoracic impedance, and cardiac tissue impedance similar to the patient's current status. A new therapy may be associated with the particular template if the previous therapy was unsatisfactory, including an anti-tachycardia pacing therapy of substantially equivalent aggression in terms of energy or coupling interval, an anti-tachycardia pacing therapy of greater aggression in terms of energy or coupling interval, and/or a cardioversion or defibrillation therapy.

Further embodiments in accordance with the present invention involve providing one or more templates representative of one or more of a patient's past tachyarrhythmia events, each of the templates associated with a therapy delivered to treat a past tachyarrhythmia event, the one or more templates including a low-rate template. A cardiac waveform is detected, and a determination is made that the cardiac waveform is indicative of a high-rate tachyarrhythmia event having one or both of a morphology and timing corresponding to the low-rate template. If the delivered therapy associated with the low-rate template was satisfactory in terminating the past tachyarrhythmia event associated with the low-rate template, it is delivered again to treat the high-rate tachyarrhythmia event. If the delivered therapy associated with the low-rate template was unsatisfactory in terminating the past ventricular tachyarrhythmia event, a therapy different from the therapy associated with the low-rate template is delivered instead.

Other embodiments in accordance with the present invention include a medical system having a cardiac therapy system configured to deliver a cardiac therapy to a patient. A detector system is configured to detect a cardiac waveform associated with a tachyarrhythmia, and a template processor, coupled to the detector system and the cardiac therapy system, is configured to provide one or more templates representative of one or more of a patient's past tachyarrhythmia events. Each of the templates is associated with a therapy to treat tachyarrhythmia events, and, if the cardiac waveform corresponds to a particular template, the template processor is configured to determine if a previous therapy associated with the particular template was satisfactory in terminating a past tachyarrhythmia event. If the previous therapy was determined satisfactory, the template processor prompts the cardiac therapy system to deliver the previous therapy. If the previous therapy was determined unsatisfactory, the previous therapy is eliminated as an option for treating a subsequent tachyarrhythmia event associated with the particular template, and the cardiac therapy system is prompted to deliver a different therapy. The cardiac therapy system may be configured to deliver an anti-tachycardia pacing therapy to the patient to treat the tachyarrhythmia and determine one or both of the effectiveness and satisfaction of the anti-tachycardia pacing therapy.

Further, a patient activity sensor may be configured to provide patient activity information associated with tachyarrhythmia episodes to the template processor. In other embodiments, a neural activity sensor is configured to provide patient neural activity information associated with tachyarrhythmia episodes to the template processor. In still further embodiments, a transthoracic impedance sensor is configured to provide patient transthoracic impedance information associated with tachyarrhythmia episodes to the template processor. In yet other embodiments, an accelerometer is configured to provide acceleration information associated with tachyarrhythmia episodes to the template processor. A cardiac tissue impedance sensing system may be configured to provide patient cardiac tissue impedance information associated with tachyarrhythmia episodes to the template processor. A hemodynamic status sensor may be configured to provide patient hemodynamic status information associated with tachyarrhythmia episodes.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
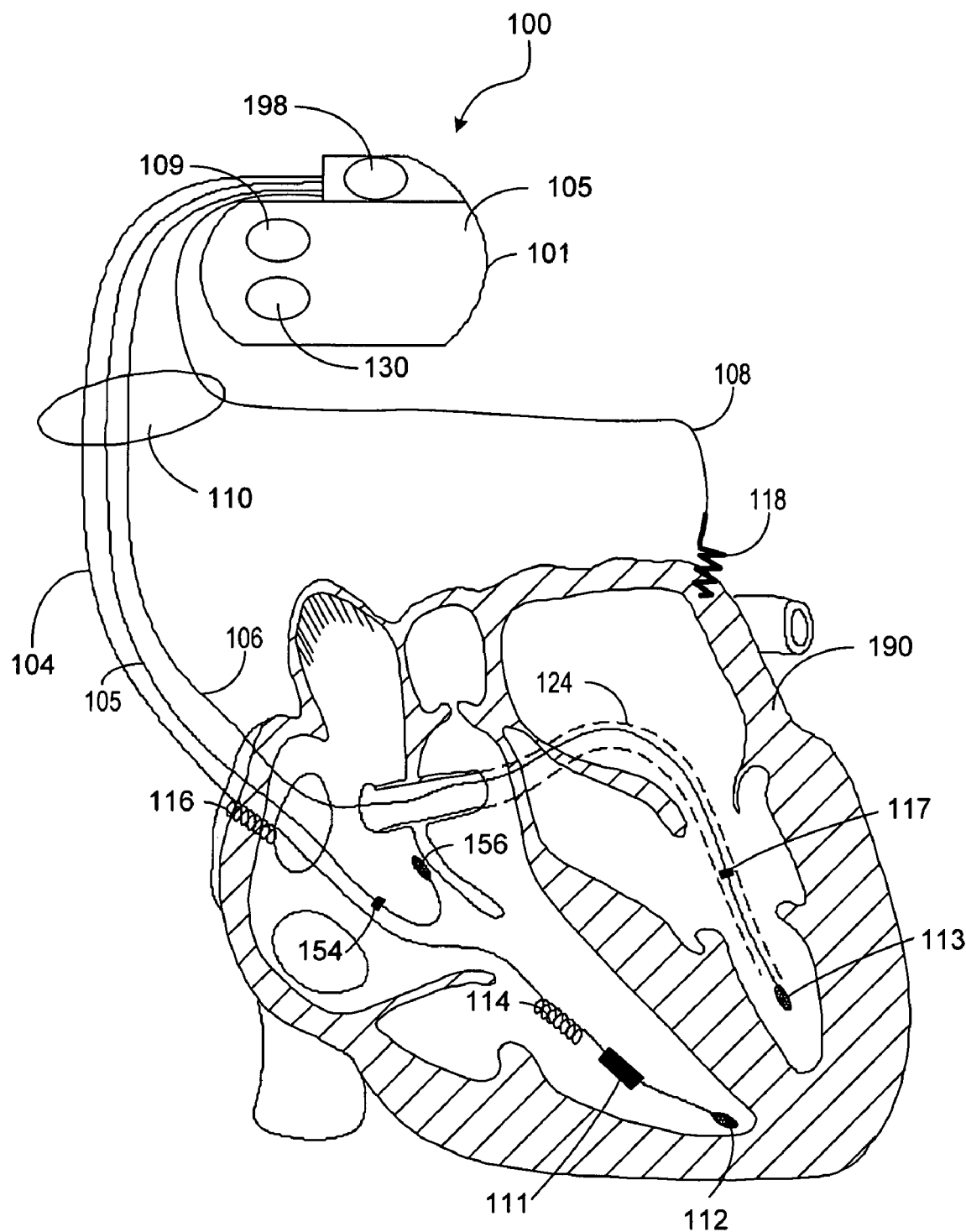
FIG. 1 is a partial view of one embodiment of an implantable medical device that may be used to implement therapy selection using patient response history in accordance with embodiments of the invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings forming a part hereof, and in which are shown by way of illustration, various embodiments by which the invention may be practiced. It is to be understood that other embodiments may be utilized, and structural and functional changes may be made without departing from the scope of the present invention.

Some current medical devices discriminate between supraventricular tachycardias (SVT) and ventricular tachycardias (VT) using cardiac waveform templates. Such devices typically detect a cardiac episode, and compare the episode in question to a normal sinus rhythm (NSR) template using an algorithm that determines a correspondence between episode information and template information. If the episode corresponds with the NSR template, the episode is diagnosed as SVT tachycardia, and therapy is withheld. In contrast, if the episode does not correspond with the NSR template, processes are typically performed to diagnose and verify the episode as ventricular tachycardia, after which therapy may be delivered. In current devices, the particular type of therapy delivered must be decided upon and programmed into the device in advance by the physician. Furthermore, if it is found that a particular type of therapy is not suitable for a patient, the physician must re-program the device during a follow-up visit such that a different type of therapy is delivered for treating the patient's subsequent ventricular tachycardias.

Some current medical devices can treat a VT by delivering a high-energy, painful shock or a low-energy, pain-free burst of anti-tachycardia pacing (ATP). Many physicians program these devices to deliver shocks for high-rate VT and reserve ATP for low-rate VT and fast atrial rhythms, such as atrial flutter. However, ATP may be safe and effective for treating high-rate VT, as well.

Furthermore, studies have shown that, for those patients for whom ATP successfully converts their first VT, there is a 99% probability that ATP will successfully convert their subsequent VTs. In contrast, studies have shown that, for those patients for whom ATP does not convert their first VT, the probability of ATP efficacy for subsequent VTs drops to only 38%.

Embodiments of methods and devices in accordance with the present invention may be implemented to adapt to changing patient conditions, medications, and/or cardiac pathology over time. Adaptation over time may possibly decrease the time to effective therapy, and increases the ratio of pain-free to painful therapy, by automatically incorporating information about that patient's prior therapy efficacy when deciding what type of therapy, if any, should be delivered to the current tachyarrhythmia episode.

In various embodiments, cardiac beats may be analyzed by examining the morphology of the electrical cardiac signal waveform. For example, a cardiac beat may be classified as a normal beat, e.g., a normally conducted SVT rhythm, by comparing the cardiac signal waveform to a template characterizing a normal beat. If the cardiac signal waveform is consistent with the template, the cardiac beat may be classified as normal. Similarly, a sensed abnormal or arrhythmic cardiac beat may be classified by comparing the abnormal cardiac signal waveform to one or more templates characterizing an abnormal beat experienced by the patient in the past. The beat may be classified as abnormal if the beat waveform does not match or correspond to a normal beat template and/or if the beat waveform matches or corresponds to an abnormal beat template. Such comparisons may be used to determine that the sensed cardiac beat is abnormal as well as to assess the type of abnormality.

A cardiac waveform template may be created and used to analyze or otherwise process a sensed cardiac signal for a variety of purposes, including, for example, arrhythmia prediction or detection. Cardiac templates may include representative waveforms and/or information derived from waveforms, such as various attributes and/or ranges of attributes of the sensed cardiac signal, including, but not limited to: timing and/or rate information, changes in QRS width, T-wave amplitude, Q-wave amplitude, QT interval, R-R intervals, interval statistics, or other intervals or attributes useful for determining a correspondence between a cardiac waveform and a template. A cardiac waveform template may be formed, for example, by identifying one or more cardiac waveform features representative of a particular cardiac beat morphology. The particular waveform features may include morphological features such as critical points, significant points, curvature, local extrema, inflection points, rise or fall times, slopes, areas above and/or below baselines, and frequency and/or wavelet coefficients, or the like.

In addition to cardiac waveform features, such as waveform morphology, templates in accordance with the present invention may include other information. Patient history to previous therapy, indicating the efficacy of previous therapy attempts for arrhythmias corresponding to a given template, may also be included. Further, other patient information, such as patient activity levels, accelerometer information, hemodynamic status (e.g., blood pressure and blood oxygen level), cardiac tissue impedance, neural activity information, transthoracic impedance, pharmacological agent type and/or level information, respiratory information (e.g., patient disordered breathing information), or other patient information may be associated with a cardiac waveform template in accordance with the present invention. Pharmacological agent type and/or level information may include a change in medications prescribed by a physician, which may alter a patient's heart rhythms, and may require adapting one or more templates to the patient's altered rhythms.

Providing this additional information as a part of the cardiac waveform template enables automated re-programming of implantable medical devices on an episode-by-episode basis, and/or in response to patient-related changes, such as a change in a patient's medication or follow-up from a physician. Information such as medication change information may be provided to an implantable medical device using an advanced patient management system, as will be further described below. Further description of cardiac waveform templates and template initiation, and updating devices and methodologies are further described in commonly owned U.S. Publication No. 2006/0074331, and U.S. Pat. Nos. 6,708,058, and 6,449,503, which are hereby incorporated herein by reference. Further description of methods and devices for determining or acquiring information that may be associated with templates in accordance with the present invention are described in commonly owned U.S. Publication Nos. 2003/0125774, 2003/0130581, 2005/0042589, and 2005/0065572, which are hereby incorporated herein by reference.

It is understood that the devices and methodologies in accordance with the present invention described with reference to ventricular tachycardia and VT templates are similarly applicable to atrial tachycardia and atrial tachycardia templates, as well as SVT/NSR and SVT/NSR templates. For SVT templates and NSR templates, the therapy associated with the template may be "none" or "withhold therapy" for example. For simplicity of explanation, and not of limitation, the description of devices and methodologies provided herein will generally be made in the context of ventricular tachycardia and VT templates.

Consider, for example, a device configured to treat VT. Once it has been confirmed that a patient has experienced at least one true VT, one or more VT templates may be generated from the prior VT episodes. A VT template may include timing and morphology information, as well as information regarding the type and efficacy of therapy used to treat the prior VT from which the template was generated. The device may use the VT template(s) to automate selection of a therapy for subsequent VTs corresponding to the template(s).

Embodiments of methods and devices in accordance with the present invention may automate this re-programming on an episode-by-episode basis. An episode in question is first compared to one or more templates indicative of a normal supra-ventricular conducted beat, such as an NSR template and/or a template indicative of fast ventricular rhythms originating in the patient's atria. If the episode corresponds to the NSR template and/or the fast atrial-originated template, it is diagnosed as SVT tachycardia (SVT) and therapy is withheld.

However, if the episode does not correspond with the one or more templates indicative of the patient's normal rhythms, the episode is then compared to the VT template(s) created from the patient's prior VT episode(s). If the current episode corresponds with any one of the VT templates, the device then checks the VT template to see if the therapy delivered to the prior VT was satisfactory. If the prior therapy was satisfactory, that same type of therapy is delivered to the current episode, regardless of the rate of the current episode.

In this way, ATP can be delivered to high-rate VTs if ATP was effective at treating similar low-rate VTs in the past. If, however, the therapy delivered to the prior VT was not effective and/or satisfactory, then a different or more aggressive therapy is delivered to the current episode. In this way, the time to effective and/or satisfactory treatment is shortened, as the device does not attempt to use a particular ATP therapy to treat a VT if that ATP therapy was not effective and/or satisfactory at treating similar VTs in the past. The time to effective treatment may be significantly shortened in accordance with an approach that does not attempt to use any type of ATP therapy to treat a VT if a prior ATP therapy was not effective and/or satisfactory at treating similar VTs in the past. In this approach, the device may immediately deliver a cardioversion or defibrillation therapy. In an alternate approach, a particular ATP therapy may be eliminated as an option for treatment if it was not satisfactory, and other ATP therapies may be attempted for subsequent events.

Embodiments of the present system illustrated herein are generally described as being implemented in a patient internal medical device (PIMD), which may operate in numerous cardioversion/defibrillation and pacing modes known in the art. Various types of single and multiple chamber PIMDs may be used to implement a number of pacing therapies as are known in the art, in addition to cardioversion/defibrillation therapies. A PIMD may implement various anti-tachyarrhythmia therapies, such as tiered anti-tachyarrhythmia therapies, which may involve performing rate-based and/or morphological tachyarrhythmia discrimination analyses.

It is understood that configurations, features, and combination of features described in the present disclosure can be implemented in a wide range of implantable or external medical devices, and that such embodiments and features are not limited to the particular devices described herein. The systems and methods described herein may be implemented in a wide variety of implantable or external diagnostic and/or therapeutic cardiac devices such as defibrillators, cardioverters, pacemakers, cardiac monitors, and resynchronizers, for example.

Although the present system is described in conjunction with an implantable cardiac defibrillator having a microprocessor-based architecture, it will be understood that the implantable cardiac defibrillator (or other device) may be implemented in any logic-based integrated circuit architecture, if desired.

In one embodiment, the cardiac rhythm management system is an implantable cardioverter/defibrillator configured as a single chamber device that operates to process cardiac waveforms according to a template methodology in accordance with the principles of the present invention. In another embodiment, the cardiac rhythm management system is an implantable cardioverter/defibrillator that is configured as a dual chamber device. In yet another embodiment, the cardiac rhythm management system is an implantable cardioverter/defibrillator configured to sense and/or provide electrical stimulation to multiple heart chambers, for example, both ventricles of the heart, as in a resynchronizer used to treat congestive heart failure (CHF).

Referring now to FIG. 1 of the drawings, there is shown one embodiment of a cardiac rhythm management system that may be used to implement tachyarrhythmia therapy selection methods of the present invention. The cardiac rhythm management system in FIG. 1 includes a PIMD 100 electrically and physically coupled to a lead system 110. The housing and/or header of the PIMD 100 may incorporate one or more electrodes 198, 109 used to provide electrical stimulation energy to the heart and to sense cardiac electrical activity. The PIMD 100 may utilize all or a portion of the PIMD housing as a can electrode 109. The PIMD 100 may include an indifferent electrode 198 positioned, for example, on the header or the housing of the PIMD 100. If the PIMD 100 includes both a can electrode 109 and an indifferent electrode 198, the electrodes 198, 109 typically are electrically isolated from each other. The PIMD 100 may also include an accelerometer 130 that may provide patient activity information and/or movement information.

The lead system 110 is used to detect electric cardiac signals produced by the heart 190 and to provide electrical energy to the heart 190 under certain predetermined conditions to treat cardiac arrhythmias. The lead system 110 may include one or more electrodes used for pacing, sensing, and/or defibrillation. In the embodiment shown in FIG. 1, the lead system 110 includes an intracardiac right ventricular (RV) lead system 104, an intracardiac right atrial (RA) lead system 105, an intracardiac left ventricular (LV) lead system 106, and an extracardiac left atrial (LA) lead system 108. The lead system 110 of FIG. 1 illustrates one embodiment that may be used in connection with the tachyarrhythmia therapy selection methodologies described herein. Other leads and/or electrodes may additionally or alternatively be used. For example, the lead system 110 may include electromyogram sensors, electroencephalogram sensors, or other sensors as desired.

The lead system 110 may include intracardiac leads 104, 105, 106 implanted in a human body with portions of the intracardiac leads 104, 105, 106 inserted into a heart 190. The intracardiac leads 104, 105, 106 include various electrodes positionable within the heart for sensing electrical activity of the heart and for delivering electrical stimulation energy to the heart, for example, pacing pulses and/or defibrillation shocks to treat various arrhythmias of the heart.

As illustrated in FIG. 1, the lead system 110 may include one or more extracardiac leads 108 having electrodes, e.g., epicardial electrodes, positioned at locations outside the heart for sensing and/or pacing one or more heart chambers.

The right ventricular lead system 104 illustrated in FIG. 1 includes an SVC-coil 116, an RV-coil 114, an RV-ring electrode 111, and an RV-tip electrode 112. The right ventricular lead system 104 extends through the right atrium 120 and into the right ventricle 119. In particular, the RV-tip electrode 112, RV-ring electrode 111, and RV-coil electrode 114 are positioned at appropriate locations within the right ventricle for sensing and delivering electrical stimulation pulses to the heart. The SVC-coil 116 is positioned at an appropriate location within the right atrium chamber of the heart 190 or a major vein leading to the right atrial chamber of the heart 190.

In one configuration, the RV-tip electrode 112 referenced to the can electrode 109 may be used to implement unipolar pacing and/or sensing in the right ventricle. Bipolar pacing and/or sensing in the right ventricle may be implemented using the RV-tip 112 and RV-ring 111 electrodes. For example, a tip-to-ring vector may be used to discriminate between VT and SVT, such as by using a template having a range of expected values of characteristics of signals sensed using this vector in some devices. In other devices, the tip-to-ring vector and the RV-coil to SVC-coil/can vector may be used to discriminate between VT and SVT. (For example, where the SVC-coil is electrically tied to the can.)

In yet another configuration, the RV-ring 111 electrode may optionally be omitted, and bipolar pacing and/or sensing may be accomplished using the RV-tip electrode 112 and the RV-coil 114, for example. The right ventricular lead system 104 may be configured as an integrated bipolar pace/shock lead. The RV-coil 114 and the SVC-coil 116 are defibrillation electrodes.

The left ventricular lead 106 includes an LV distal electrode 113 and an LV proximal electrode 117 located at appropriate locations in or about the left ventricle for pacing and/or sensing the left ventricle. The left ventricular lead 106 may be guided into the right atrium of the heart via the superior vena cava. From the right atrium, the left ventricular lead 106 may be deployed into the coronary sinus ostium, the opening of the coronary sinus. The lead 106 may be guided through the coronary sinus to a coronary vein 124 of the left ventricle. This vein is used as an access pathway for leads to reach the surfaces of the left ventricle that are not directly accessible from the right side of the heart. Lead placement for the left ventricular lead 106 may be achieved via subclavian vein access and a preformed guiding catheter for insertion of the LV electrodes 113, 117 adjacent to the left ventricle.

Unipolar pacing and/or sensing in the left ventricle may be implemented, for example, using the LV distal electrode 113 referenced to the can electrode 109. The LV distal electrode 113 and the LV proximal electrode 117 may be used together as bipolar sense and/or pace electrodes for the left ventricle. The left ventricular lead 106 and the right ventricular lead 104, in conjunction with the PIMD 100, may be used to provide cardiac resynchronization therapy such that the ventricles of the heart are paced substantially simultaneously, or in phased sequence, to provide enhanced cardiac pumping efficiency for patients suffering from chronic heart failure.

The right atrial lead 105 includes an RA-tip electrode 156 and an RA-ring electrode 154 positioned at appropriate locations in the right atrium for sensing and pacing the right atrium. In one configuration, the RA-tip 156 referenced to the can electrode 109, for example, may be used to provide unipolar pacing and/or sensing in the right atrium 120. In another configuration, the RA-tip electrode 156 and the RA-ring electrode 154 may be used to effect bipolar pacing and/or sensing.

FIG. 1 illustrates one embodiment of a left atrial lead system 108. In this example, the left atrial lead 108 is implemented as an extracardiac lead with an LA distal electrode 118 positioned at an appropriate location outside the heart 190 for sensing and pacing the left atrium. Unipolar pacing and/or sensing of the left atrium may be accomplished, for example, using the LA distal electrode 118 to the can 109 pacing vector. The left atrial lead 108 may be provided with additional electrodes used to implement bipolar pacing and/or sensing of the left atrium.

Figure 2:
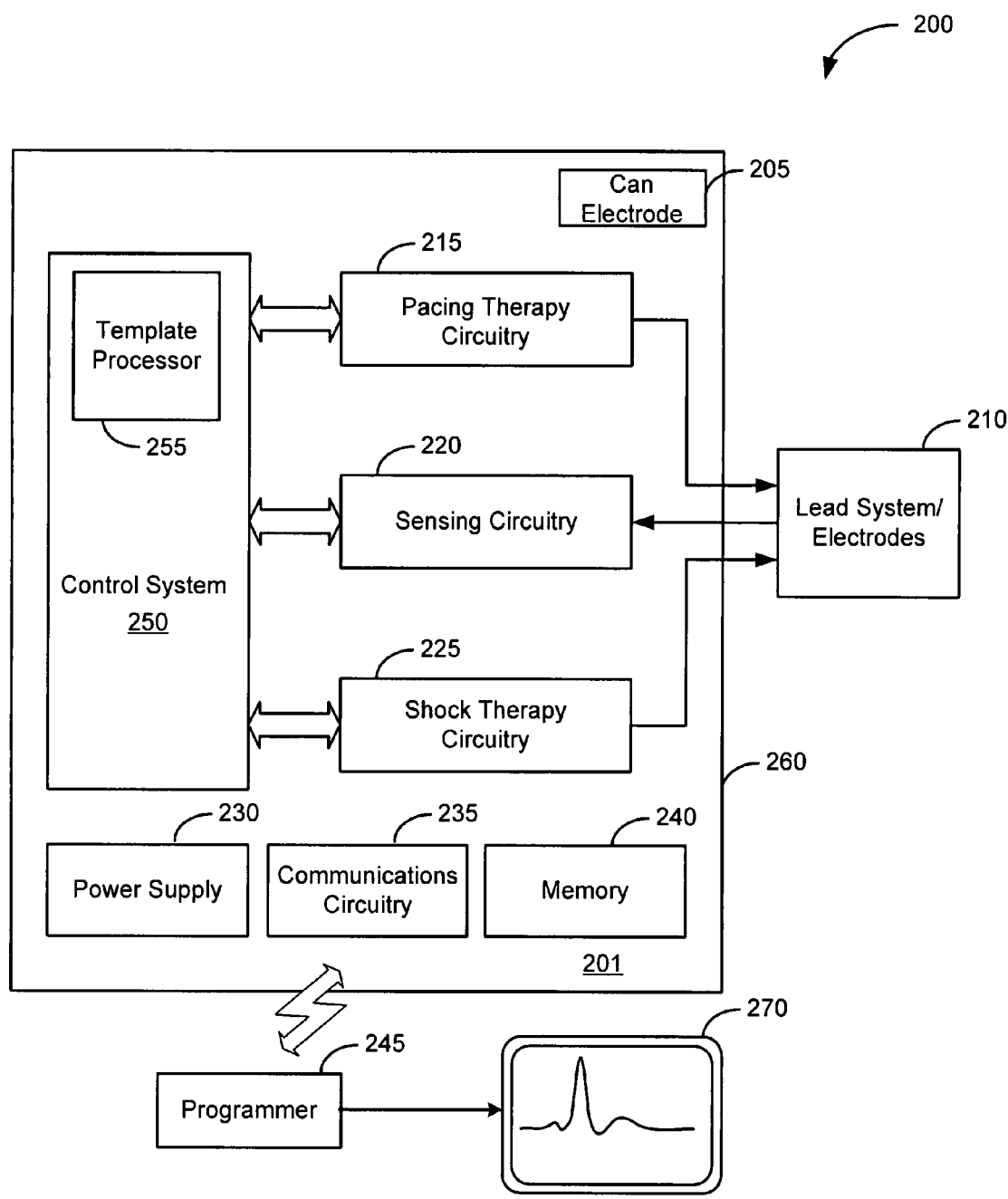
FIG. 2 is a block diagram illustrating functional components of an implantable medical device with which therapy selection using patient response history may be implemented in accordance with embodiments of the present invention.

Referring now to FIG. 2, there is shown a block diagram of an embodiment of a CRM system 200 employing a PIMD 260 suitable for implementing therapy selection methodologies of the present invention. FIG. 2 shows the CRM system 200 divided into functional blocks. There exist many possible configurations in which these functional blocks can be arranged. The example depicted in FIG. 2 is one possible functional arrangement. The CRM system 200 includes circuitry for receiving cardiac signals from a heart and delivering electrical energy in the form of pace pulses or cardioversion/defibrillation pulses to the heart.

A cardiac lead system 210 may be implanted so that cardiac electrodes contact heart tissue as described above in connection with FIG. 1. The cardiac electrodes of the lead system 210 sense cardiac signals associated with electrical activity of the heart. The sensed cardiac signals may be transmitted to a PIMD 260 through the lead system 210. The cardiac electrodes and lead system 210 may be used to deliver electrical stimulation generated by the PIMD 260 to the heart to mitigate various cardiac arrhythmias. The PIMD 260, in combination with the cardiac electrodes and lead system 210, may detect cardiac signals and deliver therapeutic electrical stimulation to any of the left and right ventricles and left and right atria, for example. A can electrode 205 coupled to a housing of the PIMD 260 may additionally be used to sense cardiac signals and deliver electrical stimulation to the heart.

In one embodiment, PIMD circuitry 201 is encased in a hermetically sealed housing suitable for implanting in a human body. Power is supplied by an electrochemical battery 230 that is housed within the PIMD 260. In one embodiment, the PIMD circuitry 201 is a programmable microprocessor-based system, including a control system 250, sensing circuit 220, pacing therapy circuit 215, shock therapy circuit 225, and memory 240. The memory 240 may be used, for example, to store template information, parameters for various pacing, defibrillation, and sensing modes, and data associated with sensed cardiac signals or other information. The parameters and data stored in the memory 240 may be used on-board for various purposes and/or transmitted via telemetry to an external programmer unit 245 or other patient-external device, as desired.

The control system 250 may be used to control various subsystems of the PIMD 260, including the pacing therapy circuit 215, the shock therapy circuitry 225, and the sensing circuitry 220. The control system 250 may also include a template processor 255 for implementing a template initiation, template generation, template updating, and methodologies for therapy selection according to embodiments of the invention.

Communications circuitry 235 allows the PIMD 260 to communicate with an external programmer unit 245 and/or other patient-external system(s). In one embodiment, the communications circuitry 235 and the programmer unit 245 use a wire loop antenna and a radio frequency telemetric link to receive and transmit signals and data between the programmer 245 and communications circuitry 235. In this manner, programming commands may be transferred to the PIMD 260 from the programmer 245 during and after implant. In addition, stored cardiac data may be transferred to the programmer unit 245 from the PIMD 260, for example.

Sensing circuitry 220 detects cardiac signals sensed at the cardiac electrodes 210. The sensing circuitry may include, for example, amplifiers, filters, A/D converters, and other signal processing circuitry. Cardiac signals processed by the sensing circuitry may be communicated to the control system 250 and to the template processor 255.

The control system 250 is coupled to the template processor 255 and uses templates created and maintained by the template processor 255 to perform various functions, including, for example, arrhythmia analysis and therapy selection. An arrhythmia analysis section of the control system 250 may compare cardiac signals detected through the sensing circuitry 220 to the templates created and maintained by the template processor 255 to detect or predict various cardiac arrhythmias, and to assist selection of appropriate therapies for the patient.

The pacing therapy circuit 215 is controlled by a pacemaker in the control system 250 and may be used to deliver pacing stimulation pulses to the heart through one or more of the cardiac electrodes, according to a pre-established pacing regimen under appropriate conditions. Also, the pacing therapy circuit 215 may deliver ATP therapy in response to VTs that correspond to templates associated with ATP.

The shock therapy circuit 225 and pacing therapy circuit 215 are coupled to an arrhythmia analysis section of the control system 250. The shock therapy circuit 225 may be used to deliver high-energy electrical stimulation to the heart to terminate or mitigate cardiac arrhythmias such as atrial or ventricular tachycardia or fibrillation detected or predicted by the control system 250 when patient history suggests that ATP is not effective and/or satisfactory, and/or when a template does not correspond to a cardiac episode.

The PIMD 260 may optionally be coupled to a display device 270 capable of displaying various information related to template creation and maintenance, and/or cardiac rhythm analysis using morphological templates, as well as other information. For example, the display device 270 may depict a graphical display of one or more detected cardiac waveforms along with the templates used to analyze or classify the detected cardiac waveforms. The display may show various data regarding the number of templates used by the PIMD, including, for example, statistics relating to the frequency particular templates were used to analyze or classify cardiac waveforms. Other uses for the display in connection with the template creation and adjustment methods of the invention are also possible.

Figure 3:
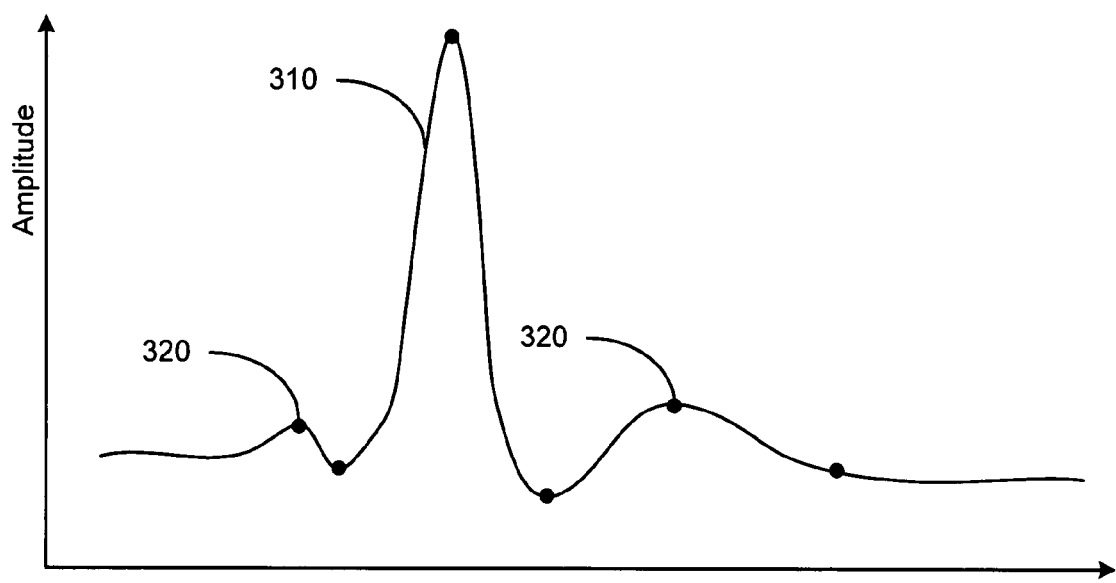
FIG. 3 is a graph illustrating a cardiac signal having cardiac waveform features useful for template creation in accordance with embodiments of the invention.

FIG. 3 illustrates a particular beat's morphology useful for template creation and correspondence in accordance with embodiments of the invention. The template may include one or more attributes characterizing a cardiac waveform representative of the particular beat morphology, for example. As illustrated in FIG. 3, a cardiac waveform 310 representing a particular beat morphology is sensed and occurrences of one or more cardiac waveform features 320 are detected. A waveform feature 320 may include a particular point of a cardiac signal waveform 310. The waveform features 320 may be identified based on various morphological aspects of the cardiac waveform, such as critical points, local extrema, inflection points, rise or fall times, slopes, areas above and/or below a baseline, and frequency and/or wavelet coefficients, or by other aspects, as is known in the art.

Figure 4:
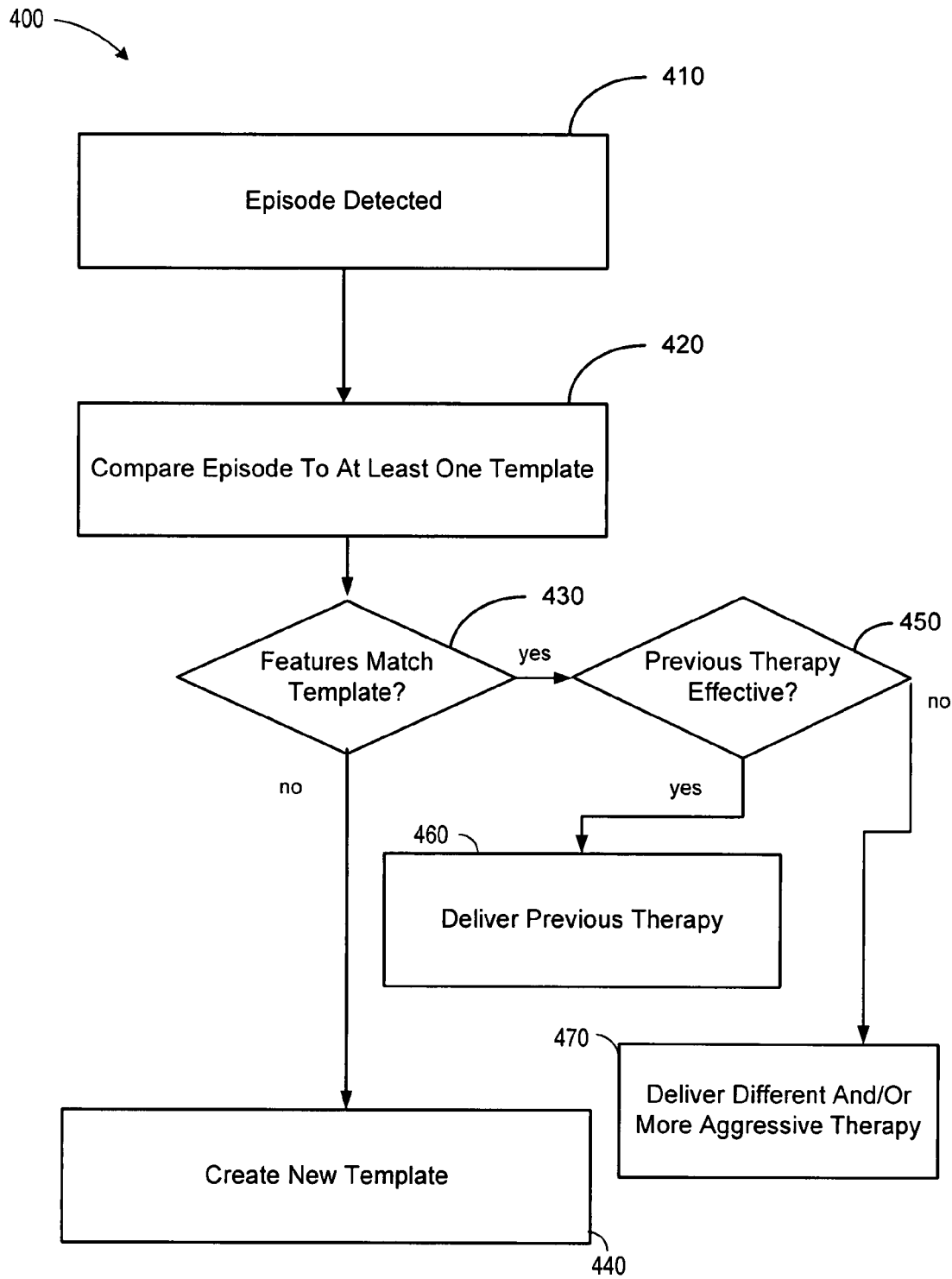
FIG. 4 is a flowchart of a method of therapy selection using patient response information in accordance with embodiments of the present invention.

FIG. 4 is a flowchart of a method 400 of therapy selection using patient response information in accordance with embodiments of the present invention. The method 400 begins with an episode 410 being detected. The episode 410 may be, for example, a rate-based or other anomaly for which discrimination is desired. Information from the episode corresponds to templates 420. The information may be a cardiac waveform encompassing a series of beats sensed from one or more electrodes, a portion of a cardiac waveform, a portion of a beat, or attributes from a cardiac waveform, as well as other information such as patient information. As an example, useful for illustrative purposes but not limiting, consider that morphological features correspond 430 to at least one of the templates 420, indicating that the episode 410 is an arrhythmia. The template 420 that corresponds to the episode 410 is then used to determine if a previous therapy was satisfactory in treating the arrhythmia. Correspondence to a template may be determined by, for example, correlation, convolution, and/or statistical analysis of cardiac waveform information.

If a previous therapy was satisfactory, for example if the template indicates that ATP was satisfactory in treating the last arrhythmia that corresponded to the template 420, then the previous therapy is delivered 460 again. If the previous therapy attempt 450 was not satisfactory, for example if the template indicates that ATP was not satisfactory in treating the last arrhythmia that corresponded to the template 420 or if the previous therapy accelerated the cardiac rhythm, then a different and/or more aggressive therapy 470 is delivered. If no templates 420 are found to correspond to 430 the current episode, then a new template may be created 440, as will be described in more detail below. Whether or not a particular therapy was satisfactory may be based upon one or more of a variety of factors, including: if the therapy was effective, if the therapy didn't take too long, if the therapy didn't cause unnecessary pain, if the therapy didn't require unnecessary energy, and/or other subjective and/or objective factors.

Figure 5:
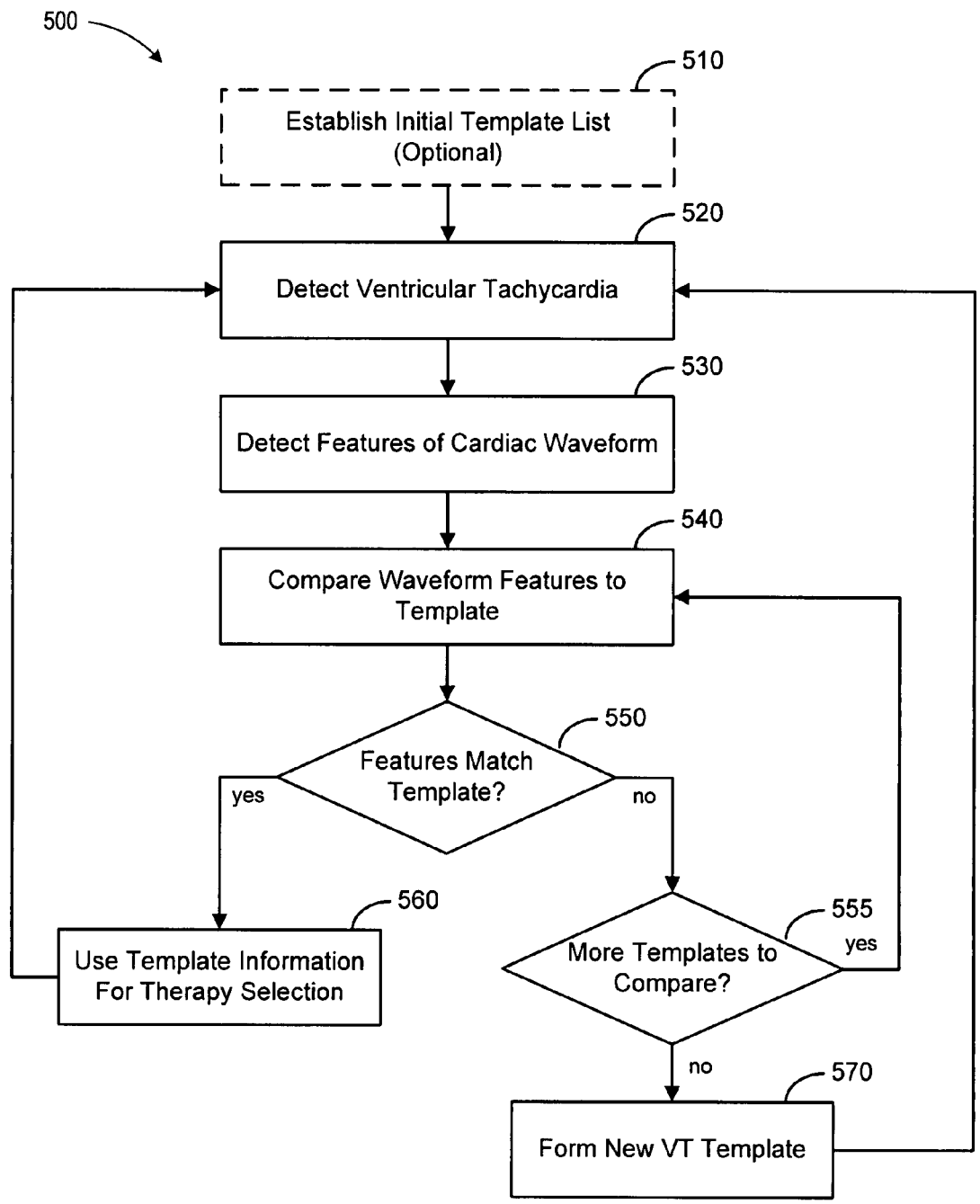
FIG. 5 is a flowchart illustrating a method of template selection and generation for therapy selection using patient response information in accordance with embodiments of the invention.

FIG. 5 is a flow chart illustrating a method 500 of template selection and generation for therapy selection using patient response information in accordance with embodiments of the invention. According to this embodiment, an initial template list comprising a list of templates representative of various cardiac beat morphologies and/or characteristics may optionally be established 510. Alternatively, new templates may be formed without an initial template list using the processes described below.

A ventricular tachycardia is sensed 520 using a cardiac waveform signal. The waveform features of the cardiac signal are detected 530 and compared 540 to each template in the template list, if any. If a predetermined number of the detected features of the cardiac waveform fall within the target ranges of the template, e.g., six of seven cardiac waveform features fall within target ranges of the template, the cardiac waveform may be classified as matching or corresponding 550 to the template. The template may then be used for therapy selection 560, based on patient therapy history information associated with the template, as described above.

If the detected waveform features do not correspond 550 to a template, the waveform features are compared to the next template until all templates have been compared 555 to the cardiac waveform features. If none of the templates correspond to the cardiac waveform features, a new template may be created 570 by, for example, extracting features of the cardiac waveform for correspondence purposes with future sensed episodes, and then associating therapy effectiveness and/or satisfaction information as therapy is delivered to the current episode. Other information may also be associated with the template, such as patient medication levels, patient activity information, and other sensor information measured at or near the time the arrhythmia occurred that may provide improved discrimination for therapy delivery selection.

Figure 6:
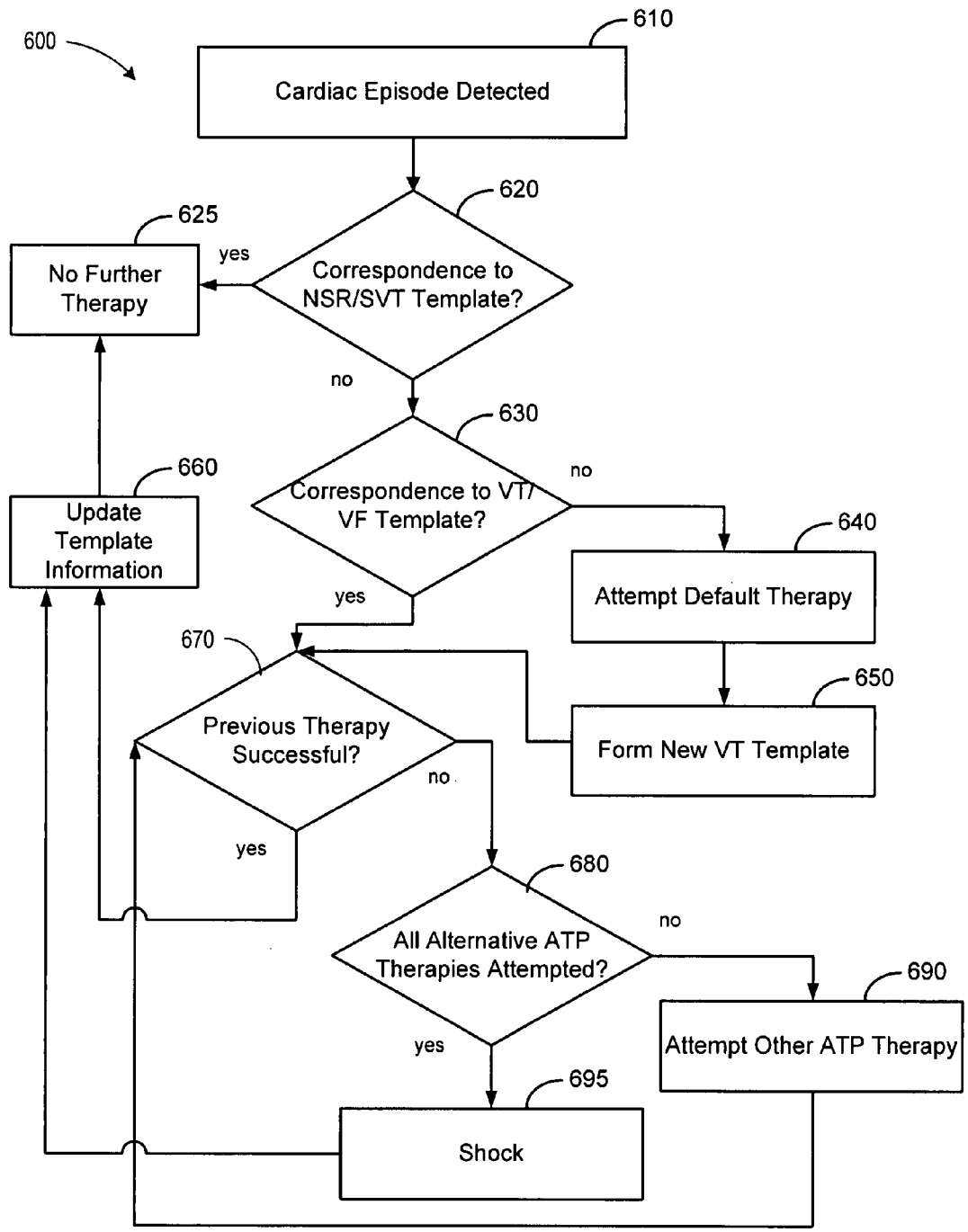
FIG. 6 is a flow chart illustrating a method of determining patient therapy response information in accordance with embodiments of the invention.

FIG. 6 is a flow chart illustrating a method 600 of determining patient therapy response information, such as therapy effectiveness and/or whether or not the therapy was satisfactory, in accordance with embodiments of the invention. The method 600 begins with an episode being detected 610. The detected episode may be, for example, a rate-based or other anomaly for which discrimination and/or characterization is desired. Information from the detected episode 610 is compared or matched 620 to one or more NSR/SVT templates to determine correspondence with the template. One method of determining that a cardiac signal may match, or correspond, to a template utilizes a correlation algorithm or other form of comparison. For example, morphological features of a signal may be measured with respect to amplitudes, inflection points, curvatures, timing of features, or other attributes. Characteristics such as timing onset, stability, variability of intervals between features of successive heartbeats, rates, and other characteristics may be included as part of a template. A template may include acceptable ranges and/or acceptable statistics of measurable features.

As an example, useful for illustrative purposes but not limiting, consider that morphological features are used to match 620 a set of templates. If the episode 610 matches or corresponds 620 to one or more NSR/SVT templates, then the episode is determined to not require therapy 625.

If the episode 610 does not match 620 to one or more NSR/SVT templates, then the morphological features of the episode 610 are compared 630 to a set of VT/VF templates. If the morphological features do not match any NSR/SVT templates 620 or any VT/VF templates 630, then a default therapy 640 is attempted, and a new VT template may be established 650. If a maximum number of templates have been reached, the method 600 may erase a template by overwriting it with new information from the latest episode 610.

In accordance with embodiments of devices that provide communications with a patient-external device, a clinician may be queried to determine if a new template is desired, or if an existing template needs to be updated or erased. This may be accomplished in coordination with an arrhythmia logbook of a PIMD during patient follow-up. Features of logbooks useful for PIMDs in accordance with the present invention are further described in commonly owned U.S. Publication Nos. 2005/0080348 and 2005/0085738, which are hereby incorporated herein by reference. Patient information acquired by such logbook systems may be incorporated or associated with VT (or atrial) templates.

In other embodiments, a template is selected for replacement using a criterion such as: templates older than a predetermined age; the oldest out of all current templates; templates that have not corresponded to an arrhythmia for a pre-determined time period; templates selected for replacement by an advanced patient management (APM) system via manual selection or via algorithmic selection; templates that have corresponded least frequently to an arrhythmia relative to other templates; templates having a pre-determined association (e.g., a drug regimen association); templates having an associated heart-rate or other identified features similar to other templates; or other template selection criteria.

After the new template 650 is established, patient history information may be acquired to fill in the necessary information of the template for future episodes. If an existing template is matched 630, or a new template 650 has been established, a check 670 determines if the previous therapy was successful and/or satisfactory. The previous therapy may be, for example, a therapy delivered in response to a prior episode, or a therapy previously attempted for the current episode. If the check 670 determines that the therapy was unsatisfactory, such as by not successfully terminating an arrhythmia, or by accelerating the heart rhythm, then an alternate ATP therapy 680 may be attempted.

If all alternative ATP therapies 680 have been attempted, then a cardioversion or defibrillation shock 695 is delivered to treat the episode 610, and the template is updated with information 660 such that the next time a cardiac signal matches that template, ATP will not be attempted, and shock therapy will be chosen. If alternative ATP therapies 680 have not been tried, then an attempt 690 is made to determine if a therapy less extreme (e.g., less painful) than cardioversion/defibrillation may correct the episode 610, and another check 670 is performed. An update 660 will occur to retain the most recent satisfactory treatment selection determined by the check 670, such that for any future episode 610 that corresponds to the template, treatment selection information will be provided for the treatment selection process.

If multiple templates are matched to the episode, then an arbitration process may be initiated to determine which of the multiple templates is to be selected. For example, the most recently used matched template with a successful therapy may be selected as the "best" template. Other criteria may be used to select between multiple matched templates, such as using the template most frequently matched to arrhythmia episodes in the past, the template having the closest rate to the current episode, the template having the highest treatment satisfaction with respect to past arrhythmia episodes, the template having the least aggressive successful treatment, or other useful criterion. The method 600 provides that a PIMD incorporating the method 600 will automatically incorporate information about that patient's prior treatment efficacy, and automatically re-program the PIMD on an episode-by-episode basis.

Figure 7:
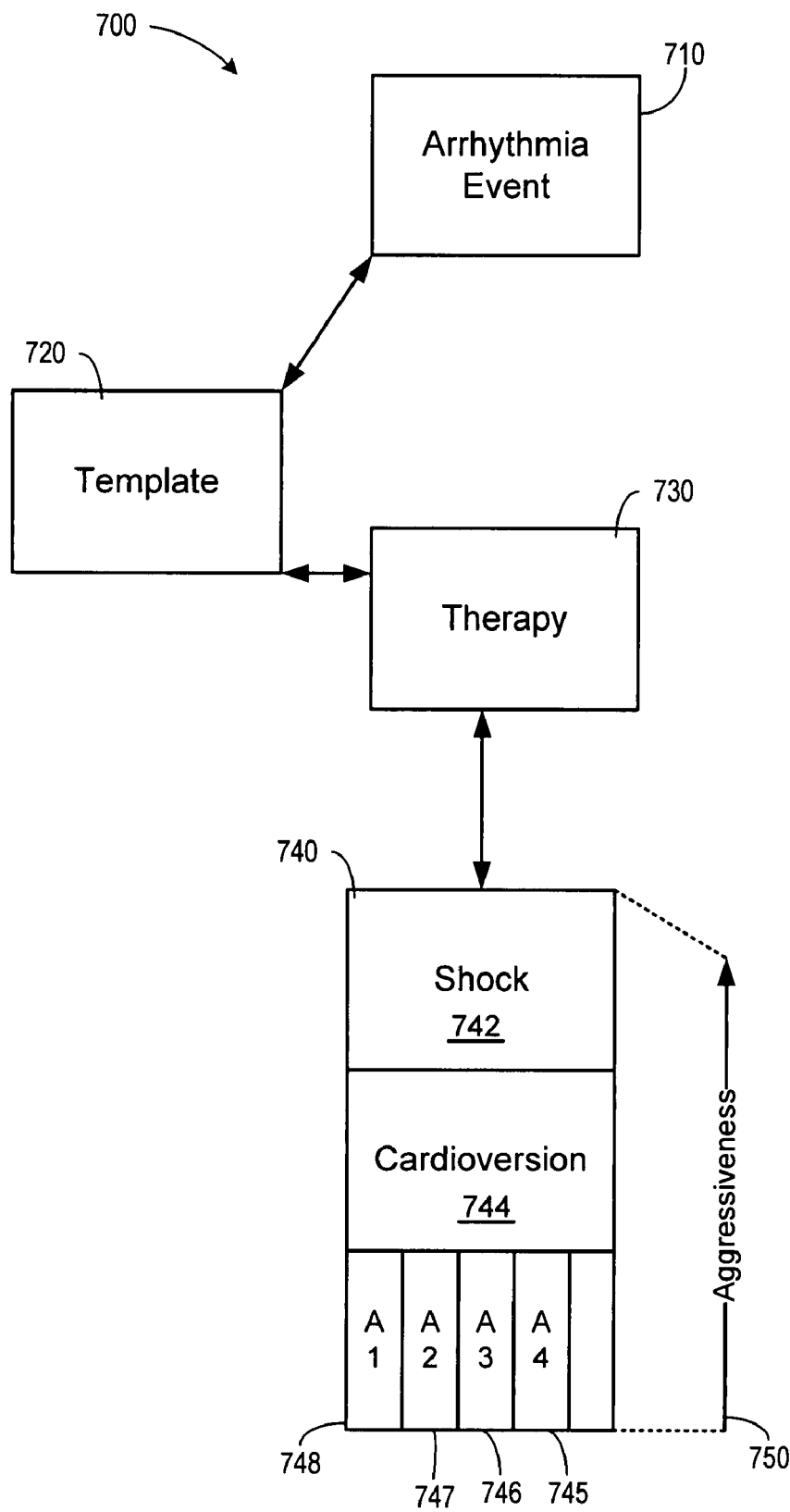
FIG. 7 is a block diagram illustrating determination of patient therapy response information in accordance with embodiments of the invention.

FIG. 7 is a block diagram illustrating a methodology for determining patient therapy response information in accordance with embodiments of the invention. An arrhythmia treatment methodology 700 may be used to associate a therapy with a template in accordance with embodiments of the present invention. The template 720 may be associated with an arrhythmia event 710, such as by corresponding to or matching the template 720, or as having been used to generate the template 720. A therapy 730 is associated with the template 720.

The therapy 730 may have been associated with the template 720 after successfully treating the arrhythmia event 710. The therapy 730 may have been delivered to a prior episode, may have been algorithmically selected via an APM system, may have been selected by a physician using a programmer or APM system, or may have been delivered to the current arrhythmia event 710. For example, an APM system may maintain a database of templates from patients other than the patient experiencing the arrhythmia event 710. The APM system may find a corresponding template, and determine what was the most satisfactory therapy for treating arrhythmias in other patients. The APM system may then select that most successful therapy as the therapy to associate with the template 720.

The therapy 730 associated with the template 720 may be a single therapy or include a number of therapies, as is shown in FIG. 7 as therapies 740. Therapies 740 include one or more shock therapies 742, which may be, for example, a maximum energy shock available from a PIMD, such as a 31 Joule shock (e.g., mono-phasic, bi-phasic, or tri-phasic shocks). Therapies 740 may also include one or more cardioversion therapies 744, which may be, for example, a lower energy shock, such as a 14 Joule shock. Therapies 740 may also include several ATP therapies, such as ATP1 therapy 748, ATP2 therapy 747, ATP3 therapy 746, and ATP4 therapy 745. The ATP therapies 745-748 may be all different therapies having the same energy level, for example. An aggressiveness level 750 indicates that ATP therapies 745-748 are considered less aggressive than the cardioversion therapy 744, which is less aggressive than shock therapy 742.

When a template is originated, an initial arrhythmia may be treated with a lower aggression therapy first, and different therapies, increasing in aggressiveness, may be attempted until a therapy is successful at treating the arrhythmia. The lowest aggressiveness therapy that successfully treats the arrhythmia may then be associated with the template for future reference. This corresponds to a hierarchical approach, where therapies are attempted in an ordered fashion according to an aggressiveness hierarchy. A method for generating and selecting hierarchies of therapies is described in U.S. Publication No. 2004/0167579A1, which is hereby incorporated herein by reference.

In other embodiments, a more aggressive therapy may be used when a cardiac waveform is sensed that does not match or correspond to any template, and the waveform may be saved or transmitted for assessment by a clinician to determine if a template should be made, or if another therapy should be associated with that type of cardiac waveform. For example, upon initial determination of a new arrhythmia, a high-energy shock, an initial ATP therapy, or other default therapy, may be used and the cardiac waveform may be designated for review to determine which therapy, if any, should be associated with subsequent corresponding arrhythmias.

In other embodiments, a heuristic approach is used where no hierarchy is established. For example, the last therapy delivered may be repeated, or a therapy may be randomly selected from available therapies until a satisfactory therapy is determined. Satisfaction with a therapy may include parameters other than just effectiveness such as, for example, time to effectiveness, patient pain, patient loss of consciousness, or other satisfaction criteria.

Figure 8:
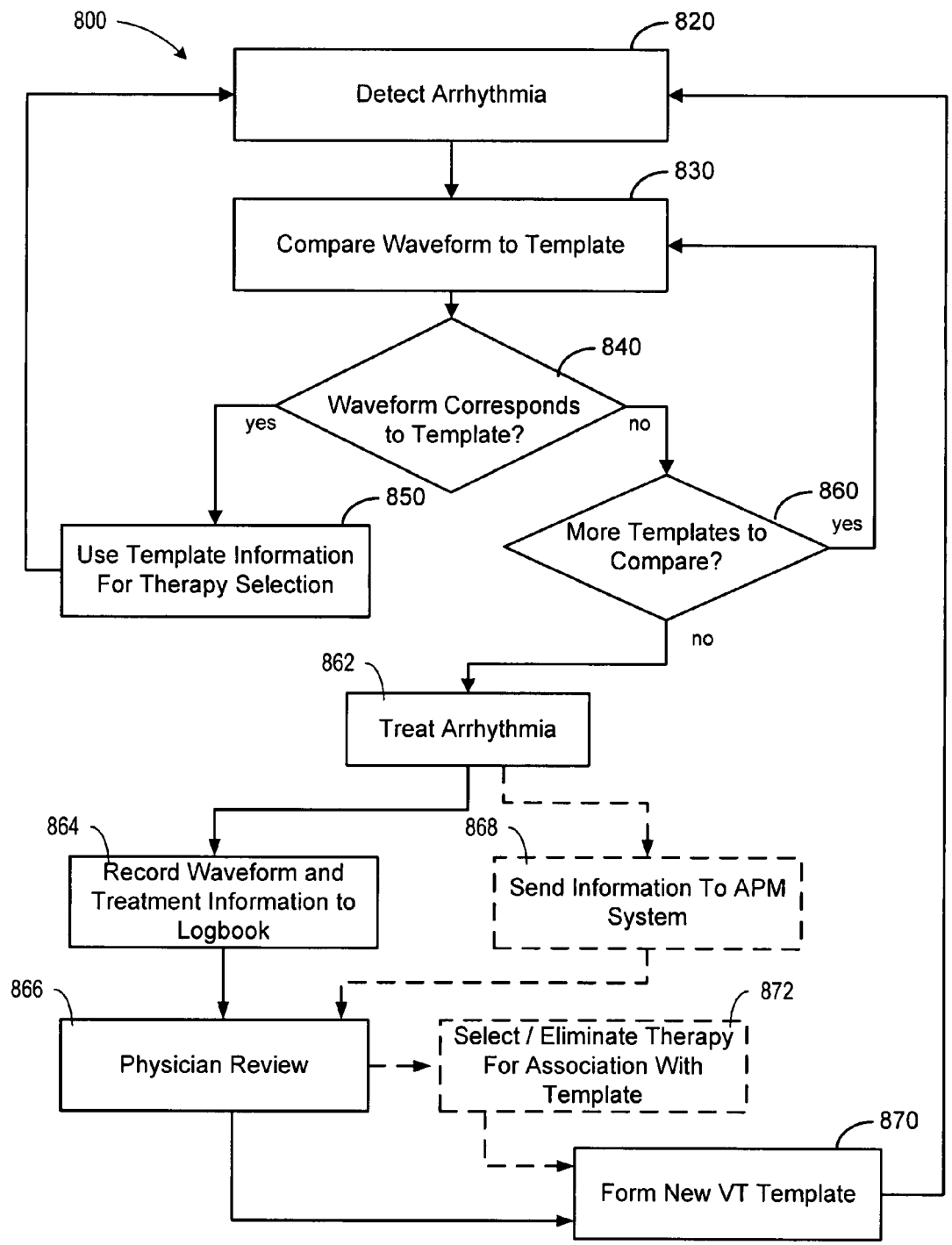
FIG. 8 is a flow chart illustrating a method of initializing templates in accordance with embodiments of the invention.

FIG. 8 is a flow chart illustrating a method 800 of template selection and generation for therapy selection using patient response information in accordance with embodiments of the invention. According to this embodiment, templates are established by a physician selecting a cardiac waveform for template creation after reviewing a logbook of arrhythmia episodes and treatments. An arrhythmia is detected 820 using a cardiac waveform signal. The waveform is compared 830 to each template in the template list, if any. If the cardiac waveform corresponds to a template 840, the template may then be used for therapy selection 850, based on patient therapy history information associated with the template, as described above.

If the detected waveform does not correspond to the template 840, the waveform is compared to the next template until all templates have been compared 860 to the cardiac waveform. If none of the templates 840 correspond to the cardiac waveform, the arrhythmia is treated 862. Treatment 862 may be performed using the method 700, for example. Alternatively, the arrhythmia may be treated using a cardioversion and/or defibrillation methodology, or other predetermined default treatment. The cardiac waveform, and any associated information, such as treatment history, and/or other sensor information is recorded 864, such as by using a memory or logbook feature.

The cardiac waveform and associated information is then reviewed by a clinician, such as a physician 866. The physician 866 may select particular recorded waveforms for template generation 870. The selected waveforms then have templates formed 870, and a therapy is associated with the template. When reviewing the recording 864, the physician may select or eliminate from consideration one or more therapies 872 for association with the template. For example, the physician may determine that a defibrillation was performed on a cardiac waveform that may be treated by ATP. The physician may select ATP therapy as the associated therapy for the template 870, such that the next cardiac waveform that matches or corresponds to the template 870 is treated with ATP therapy. The physician may also select an order of multiple therapies to try, for example.

The physician may select an ATP therapy of similar aggression, but different coupling interval. The coupling interval is the point in time during the cardiac cycle at which the pacing pulse should be delivered. A typical coupling interval is 80%, with the pacing pulse delivered at a time predicted to be 80% between the last R wave and the next R wave. ATP with a coupling interval of 70% may deliver the same energy to the patient as ATP with a coupling interval of 80%. However, shorter coupling intervals are considered to be more aggressive, as there is more risk that the pacing pulse could accelerate the rhythm instead of terminating the rhythm.

Other information may also be associated with the template, such as patient medication levels, patient activity information, and other information provided by the physician that may provide improved discrimination for therapy delivery selection. The physician may provide the information during a follow-up office visit, using a programmer, for example. The physician or a clinician may also perform the method 800 remotely, such as by using an advanced patient management (APM) system 868 as will be described below. In other embodiments, the APM system may incorporate an artificial intelligence system or other programming to remotely perform methods of template generation, initialization, updating, therapy association, and/or selection in accordance with the present invention.

Devices and methods useful for determining or acquiring information that may be associated with templates in accordance with embodiments of the present invention are further described in commonly owned co-pending U.S. Publication Nos. 2003/0109902, 2005/0081847, and 2006/0047333, which are hereby incorporated herein by reference.

Figure 9:
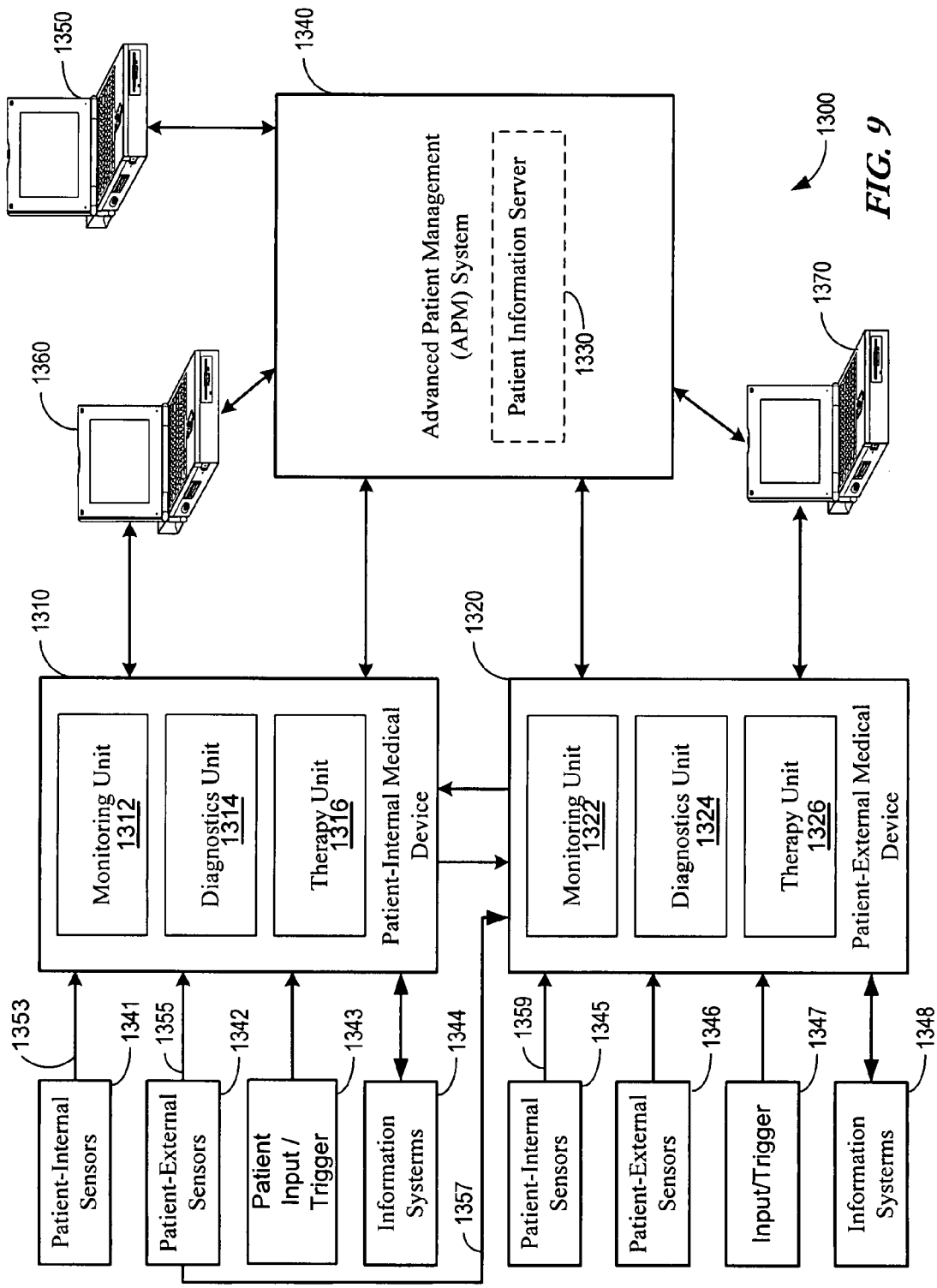
FIG. 9 is a block diagram of a medical system that may be used to implement arrhythmia therapy selection using patient therapy response information and other patient information in accordance with embodiments of the present invention.

Referring now to FIG. 9, a PIMD of the present invention may be used within the structure of an APM system 1300. The APM system 1300 allows physicians and/or other clinicians to remotely and automatically monitor cardiac and respiratory functions, as well as other patient conditions. The APM system 1300 may also be used to provide information to the PIMD for incorporation into templates, such as medication information or other patient information useful in accordance with the present invention. The APM system 1300 may also be used to select portions of cardiac waveforms for which templates are desired. The APM system 1300 may also be used to select or eliminate therapies associated with templates. In one example, a PIMD implemented as a cardiac pacemaker, defibrillator, or resynchronization device may be equipped with various telecommunications and information technologies that enable real-time data collection, diagnosis, and treatment of the patient.

Various PIMD embodiments described herein may be used in connection with advanced patient management. Methods, structures, and/or techniques described herein, which may be adapted to provide for remote patient/device monitoring, diagnosis, therapy, or other APM related methodologies, may incorporate features of one or more of the following references: U.S. Pat. Nos. 6,221,011; 6,270,457; 6,277,072; 6,280,380; 6,312,378; 6,336,903; 6,358,203; 6,368,284; 6,398,728; and 6,440,066, which are hereby incorporated herein by reference.

As is illustrated in FIG. 9, the medical system 1300 may be used to implement template generation, template updating, template initialization, template selection, patient measuring, patient monitoring, patient diagnosis, patient therapy, therapy selection, and/or therapy elimination in accordance with embodiments of the invention. The medical system 1300 may include, for example, one or more patient-internal medical devices 1310, such as a PIMD, and one or more patient-external medical devices 1320, such as a monitor or signal display device. Each of the patient-internal 1310 and patient-external 1320 medical devices may include one or more of a patient monitoring unit 1312, 1322, a diagnostics unit 1314, 1324, and/or a therapy unit 1316, 1326.

The patient-external medical device 1320 performs monitoring, and/or diagnosis and/or therapy functions external to the patient (i.e., not invasively implanted within the patient's body). The patient-external medical device 1320 may be positioned on the patient, near the patient, or in any location external to the patient.

The patient-internal and patient-external medical devices 1310, 1320 may be coupled to one or more sensors 1341, 1342, 1345, 1346, patient input/trigger devices 1343, 1347, and/or other information acquisition devices 1344, 1348. The sensors 1341, 1342, 1345, 1346, patient input/trigger devices 1343, 1347, and/or other information acquisition devices 1344, 1348 may be employed to detect conditions relevant to the monitoring, diagnostic, and/or therapeutic functions of the patient-internal and patient-external medical devices 1310, 1320.

The medical devices 1310, 1320 may each be coupled to one or more patient-internal sensors 1341, 1345 that are fully or partially implantable within the patient. The medical devices 1310, 1320 may also be coupled to patient-external sensors positioned on, near, or in a remote location with respect to the patient. The patient-internal and patient-external sensors are used to sense conditions, such as physiological or environmental conditions, that affect the patient.

The patient-internal sensors 1341 may be coupled to the patient-internal medical device 1310 through one or more internal leads 1353. Still referring to FIG. 9, one or more patient-internal sensors 1341 may be equipped with transceiver circuitry to support wireless communications between the one or more patient-internal sensors 1341 and the patient-internal medical device 1310 and/or the patient-external medical device 1320. The patient-internal sensors 1345 may be coupled to the patient-external medical device 1320 through a wireless connection 1359, and/or using communications between the patient-internal medical device 1310 and the patient-external medical device 1320, or may be coupled using a wire or other communications channel.

The patient-external sensors 1342 may be coupled to the patient-internal medical device 1310 through one or more internal leads 1355. Patient-external sensors 1342 may communicate with the patient-internal medical device 1310 wirelessly. Patient-external sensors 1342 may be coupled to the patient-external medical device 1320 through one or more leads 1357 or through a wireless link.

In an embodiment of the present invention, the patient-external medical device 1320 includes a visual display configured to concurrently display non-electrophysiological signals and intracardiac electrogram signals. For example, the display may present the information visually. The patient-external medical device 1320 may also, or alternately, provide signals to other components of the medical system 1300 for presentation to a clinician, whether local to the patient or remote to the patient.

Referring still to FIG. 9, the medical devices 1310, 1320 may be connected to one or more information acquisition devices 1344, 1348, such as a database that stores information useful in connection with the monitoring, diagnostic, or therapy functions of the medical devices 1310, 1320. For example, one or more of the medical devices 1310, 1320 may be coupled through a network to a patient information server 1330.

The input/trigger devices 1343, 1347 are used to allow the physician, clinician, and/or patient to manually trigger and/or transfer information to the medical devices 1310, 1320 and/or from the APM system 1340 and/or patient-external medical device 1320 back to the patient-internal device 1310. The input/trigger devices 1343, 1347 may be particularly useful for inputting information concerning patient perceptions, such as a perceived cardiac event, how well the patient feels, and other information not automatically sensed or detected by the medical devices 1310, 1320. For example, the patient may trigger the input/trigger device 1343 upon perceiving a cardiac event. The trigger may then initiate the recording of cardiac signals and/or other sensor signals in the patient-internal device 1310. Later, a clinician may trigger the input/trigger device 1347, initiating the transfer of the recorded cardiac and/or other signals from the patient-internal device 1310 to the patient-external device 1320 for display and diagnosis.

In one embodiment, the patient-internal medical device 1310 and the patient-external medical device 1320 may communicate through a wireless link between the medical devices 1310, 1320. For example, the patient-internal and patient-external devices 1310, 1320 may be coupled through a short-range radio link, such as Bluetooth, IEEE 802.11, and/or a proprietary wireless protocol. The communications link may facilitate uni-directional or bi-directional communication between the patient-internal 1310 and patient-external 1320 medical devices. Data and/or control signals may be transmitted between the patient-internal 1310 and patient-external 1320 medical devices to coordinate the functions of the medical devices 1310, 1320.

In another embodiment, patient data may be downloaded from one or more of the medical devices periodically or on command, and stored at the patient information server 1330. The physician and/or the patient may communicate with the medical devices and the patient information server 1330, for example, to acquire patient data or to initiate, terminate, or modify recording and/or therapy.

The data stored on the patient information server 1330 may be accessible by the patient and the patient's physician through one or more terminals 1350, e.g., remote computers located in the patient's home or the physician's office. The patient information server 1330 may be used to communicate to one or more of the patient-internal and patient-external medical devices 1310, 1320 to provide remote control of the monitoring, diagnosis, and/or therapy functions of the medical devices 1310, 1320.

In one embodiment, the patient's physician may access patient data transmitted from the medical devices 1310, 1320 to the patient information server 1330. After evaluation of the patient data, the patient's physician may communicate with one or more of the patient-internal or patient-external devices 1310, 1320 through an APM system 1340 to initiate, terminate, or modify the monitoring, diagnostic, and/or therapy functions of the patient-internal and/or patient-external medical systems 1310, 1320.

In another embodiment, the patient-internal and patient-external medical devices 1310, 1320 may not communicate directly, but may communicate indirectly through the APM system 1340. In this embodiment, the APM system 1340 may operate as an intermediary between two or more of the medical devices 1310, 1320. For example, data and/or control information may be transferred from one of the medical devices 1310, 1320 to the APM system 1340. The APM system 1340 may transfer the data and/or control information to another of the medical devices 1310, 1320.

In one embodiment, the APM system 1340 may communicate directly with the patient-internal and/or patient-external medical devices 1310, 1320. In another embodiment, the APM system 1340 may communicate with the patient-internal and/or patient-external medical devices 1310, 1320 through medical device programmers 1360, 1370 respectively associated with each medical device 1310, 1320. As was stated previously, the patient-internal medical device 1310 may take the form of an implantable PIMD.

Medical devices and methods that select tachyarrhythmia therapy based on previous patient therapy responses in accordance with the present invention may be used in combination with methods of tachyarrhythmia discrimination using arrhythmia memory, which is further described in commonly-owned co-pending U.S. Publication No. 2006/0111643, which is hereby incorporated herein by reference, and/or in combination with methods of generating templates based on previous patient therapy responses, which is further described in commonly-owned co-pending U.S. Publication No. 2006/0111747, which is hereby incorporated herein by reference.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method, comprising:
providing one or more templates representative of one or more of a patient's past tachyarrhythmia events, the one or more templates associated in memory with a therapy to treat tachyarrhythmia events;
detecting a cardiac waveform;
matching a particular template of the one or more templates with the cardiac waveform;
delivering the therapy based on the match between the particular template and the cardiac waveform; and
determining whether the therapy was unsatisfactory in terminating an arrhythmia associated with the particular template and, if the therapy is determined unsatisfactory, eliminating the therapy as an option for treating a subsequent tachyarrhythmia event associated in memory with the particular template and associating in memory the particular template with a new therapy.

2. The method of claim 1, wherein if the therapy was an antitachycardia pacing therapy determined to be unsatisfactory in terminating the tachyarrhythmia event, eliminating delivery of the antitachycardia pacing therapy as an option for treating a subsequent tachyarrhythmia event and associating one or more of a cardioversion, a defibrillation therapy, or an alternate anti-tachycardia pacing therapy with the particular template.

3. The method of claim 1, wherein the matching between the cardiac waveform and the particular template is a correspondence in terms of morphology.

4. The method of claim 1, wherein the matching between the cardiac waveform and the particular template is a correspondence in terms of timing.

5. The method of claim 1, wherein the matching between the cardiac waveform and the particular template is a correspondence in terms of a) drug regimen and morphology or b) drug regimen and timing.

6. The method of claim 1, comprising adding a new template to the one or more templates by replacing an oldest template of the one or more templates with the new template.

7. The method of claim 1, comprising associating one or more of medication information, neural activity information, patient activity information, hemodynamic status information, cardiac tissue impedance information, and transthoracic impedance information with the one or more templates.

8. The method of claim 1, comprising deleting a particular template of the one or more templates if the particular template is older than a predetermined age, or has not matched to a cardiac waveform for a predetermined time, or has matched to past arrhythmias least frequently relative to other templates, or represents a heart-rate similar to other existing templates.

9. The method of claim 1, comprising deleting a particular template of the one or more templates if the particular template is associated with a drug regimen that no longer matches the patient's current drug regimen.

10. The method of claim 1, wherein the detected cardiac waveform is indicative of an arrhythmia in the ventricles, of ventricular or supra-ventricular origin.

11. The method of claim 1, wherein the detected cardiac waveform is indicative of an arrhythmia in the atria.

12. The method of claim 1, further comprising arbitrating between two or more templates if the cardiac waveform matches two or more templates.

13. The method of claim 1, further comprising, if the cardiac waveform matches two or more templates:
selecting a template of the two or more templates associated with a treatment satisfactory in terminating the tachyarrhythmia event, and delivering its associated tachyarrhythmia therapy; or
selecting a most recently used or generated template associated with a treatment satisfactory in terminating the tachyarrhythmia event, and delivering its associated tachyarrhythmia therapy; or
selecting the most frequently matched template associated with a treatment satisfactory in terminating the tachyarrhythmia event, and delivering its associated tachyarrhythmia therapy; or
selecting the template associated with a treatment satisfactory in terminating the tachyarrhythmia event whose rate information most closely corresponds to the detected cardiac waveform, and delivering its associated tachyarrhythmia therapy; or
selecting the template associated with one or more of a patient's drug regimen, neural activity, patient activity, hemodynamic state, transthoracic impedance, and cardiac tissue impedance similar to the patient's current status.

14. The method of claim 1, wherein the new therapy comprises an anti-tachycardia pacing therapy of substantially equivalent aggression in terms of energy or coupling interval.

15. The method of claim 1, wherein the new therapy comprises an anti-tachycardia pacing therapy of greater aggression in terms of energy or coupling interval.

16. The method of claim 1, wherein the new therapy comprises a cardioversion or defibrillation therapy.

17. A medical system, comprising:
a cardiac therapy system configured to deliver a cardiac therapy to a patient;
a detector system configured to detect a cardiac waveform associated with a tachyarrhythmia;
therapy delivery circuitry configured to deliver one or more therapies to treat tachyarrhythmia events; and a template processor and memory coupled to the detector system and the cardiac therapy system, the template processor and memory configured to store one or more templates representative of one or more of a patient's past tachyarrhythmia events, the one or more templates associated in memory with the one or more therapies, match a particular template of the one or more templates with the cardiac waveform, facilitate delivery of a therapy of the one or more therapies by the therapy delivery circuitry based on the match between the particular template and the cardiac waveform, determine whether the therapy was satisfactory in terminating an arrhythmia associated with the particular template and if the therapy is determined unsatisfactory, eliminate the therapy as an option for treating a subsequent tachyarrhythmia event associated with the particular template and associate the particular template with a new therapy.

18. The system of claim 17, wherein the cardiac therapy system is configured to deliver an anti-tachycardia pacing therapy to the patient to treat the tachyarrhythmia and determine one or both of the effectiveness and satisfaction of the anti-tachycardia pacing therapy.

19. The system of claim 17, comprising a patient activity sensor configured to provide patient activity information associated with tachyarrhythmia episodes to the template processor.

20. The system of claim 17, comprising a neural activity sensor configured to provide patient neural activity information associated with tachyarrhythmia episodes to the template processor.

21. The system of claim 17, comprising a transthoracic impedance sensor configured to provide patient transthoracic impedance information associated with tachyarrhythmia episodes to the template processor.

22. The system of claim 17, comprising an accelerometer configured to provide acceleration information associated with tachyarrhythmia episodes to the template processor.

23. The system of claim 17, comprising a cardiac tissue impedance sensing system configured to provide patient cardiac tissue impedance information associated with tachyarrhythmia episodes to the template processor.

24. The system of claim 17, comprising a hemodynamic status sensor configured to provide patient hemodynamic status information associated with tachyarrhythmia episodes.

* * * * *